United States Patent [19]
Froggatt

[11] Patent Number: 5,404,743
[45] Date of Patent: Apr. 11, 1995

[54] PULSED PHASE LOCKED LOOP STRAIN MONITOR

[75] Inventor: Mark E. Froggatt, Prince George, Va.

[73] Assignee: The United States of America as represented by the Administrator of the National Aeronautics and Space Administration, Washington, D.C.

[21] Appl. No.: 105,161

[22] Filed: Aug. 12, 1993

[51] Int. Cl.⁶ .............................................. F16B 13/02
[52] U.S. Cl. ........................................ 73/1 B; 73/597
[58] Field of Search .......................... 73/1 B, 597, 761; 331/64, DIG. 2; 367/125

[56] References Cited

U.S. PATENT DOCUMENTS 4,177,731 10/1978 Heyman ................................. 73/761
4,297,649 10/1981 Sbuelz et al. .
4,363,242 12/1982 Heyman .
4,752,917 6/1988 Dechape .
4,754,186 6/1988 Choperena et al. .
4,833,460 6/1989 Heyman et al. .
4,958,520 9/1990 Trommler et al. .
4,975,930 12/1990 Shaw .
5,150,620 9/1992 Allison .

*Primary Examiner*—Robert Raevis
*Attorney, Agent, or Firm*—Kimberly A. Chasteen

[57] ABSTRACT

A pulse phase locked loop system according to the present invention is described. A frequency generator such as a voltage controlled oscillator (VCO) generates an output signal and a reference signal having a frequency equal to that of the output signal. A transmitting gate gates the output frequency signal and this gated signal drives a transmitting transducer which transmits an acoustic wave through a material. A sample/hold samples a signal indicative of the transmitted wave which is received by a receiving transducer. Divide-by-n counters control these gating and sampling functions in response to the reference signal of the frequency generator. Specifically, the output signal is gated at a rate of F/h, wherein F is the frequency of the output signal and h is an integer; and the received signal is sampled at a delay of F/n wherein n is an integer.

5 Claims, 6 Drawing Sheets

PULSED PHASE LOCKED LOOP STRAIN MONITOR

ORIGIN OF THE INVENTION

The invention described herein was made by an employee of the United States Government and may be used by or for the Government for governmental purposes without the payment of any royalties thereon or therefor.

CROSS-REFERENCE TO RELATED APPLICATIONS

This application is related to U.S. Pat. No. 5,237,515, issued Aug. 17, 1993, now U.S. Pat. No. 5,237,516 and U.S. Pat. No. 5,150,620, issued Sep. 29, 1992, the specifications of which are hereby incorporated by reference.

BACKGROUND OF THE INVENTION

1. Technical Field of the Invention

The present invention relates generally to a pulsed phase locked loop and more particularly to improvements in a pulsed phase locked loop to measure small changes in the ultrasonic path length of a material and accordingly calculate stress in the material.

2. Discussion of the Related Art

A pulsed phase locked loop (P2L2) strain monitor is described in U.S. Pat. No. 4,363,242 to Heyman and is used to nondestructively measure the load on a bearing member such as a bolt, connector, etc. The components and operation of this P2L2 monitor are discussed in greater detail below. A problem of this monitor is that a low pass filter located after a mixer phase detector causes errors in the phase measurement due to the step response of the low pass filter. Although this induced error is not significant enough to prevent the P2L2 monitor from tracking small changes in frequency, it does corrupt the spacing of the lock points in such a way that transducer calibration is not possible since the calibration requires reacquisition of the same lock point for each transducer. The recertification of a loaded member described in the related applications depends on the reacquisition of certain specified lock points. In addition, use of a voltage controlled oscillation (VCO) slows the speed of data acquisition, prevents the system from being automated, and increases the complexity of the monitor by requiring a very accurate, e.g., within 1 Hz frequency measurement.

OBJECTS OF THE INVENTION

It is accordingly an object of the present invention to reduce errors in phase measurement of a P2L2 system.

It is another object of the present invention to eliminate the step response of a low pass filter in a P2L2 system.

It is a further object of the present invention to permit transducer calibration.

It is another object of the present invention to permit consistent reacquisition of the same lock point, thereby allowing for recertification of loaded members.

It is another object of the present invention to increase the data acquisition speed of a P2L2 system.

It is a further object of the present invention to accomplish the foregoing objects in a relatively simple manner.

Additional objects and advantages of the present invention are apparent from the specification and drawings which follow.

SUMMARY OF THE INVENTION

The foregoing and additional objects are accomplished by a pulse phase locked loop system according to the present invention. A frequency generator such as a voltage controlled oscillator (VCO) generates an output signal and a reference signal having a frequency equal to that of the output signal. A transmitting gate gates the output frequency signal and this gated signal drives a transmitting transducer which transmits an acoustic wave through a material. A sample/hold samples a signal indicative of the transmitted wave which is received by a receiving transducer. Divide-by-n counters control these gating and sampling functions in response to the reference signal of the frequency generator. Specifically, the output signal is gated at a rate of F/h, wherein F is the frequency of the output signal and h is an integer; and the received signal is sampled a specified integer number of periods later.

DETAILED DESCRIPTION OF THE INVENTION

Figure 1:
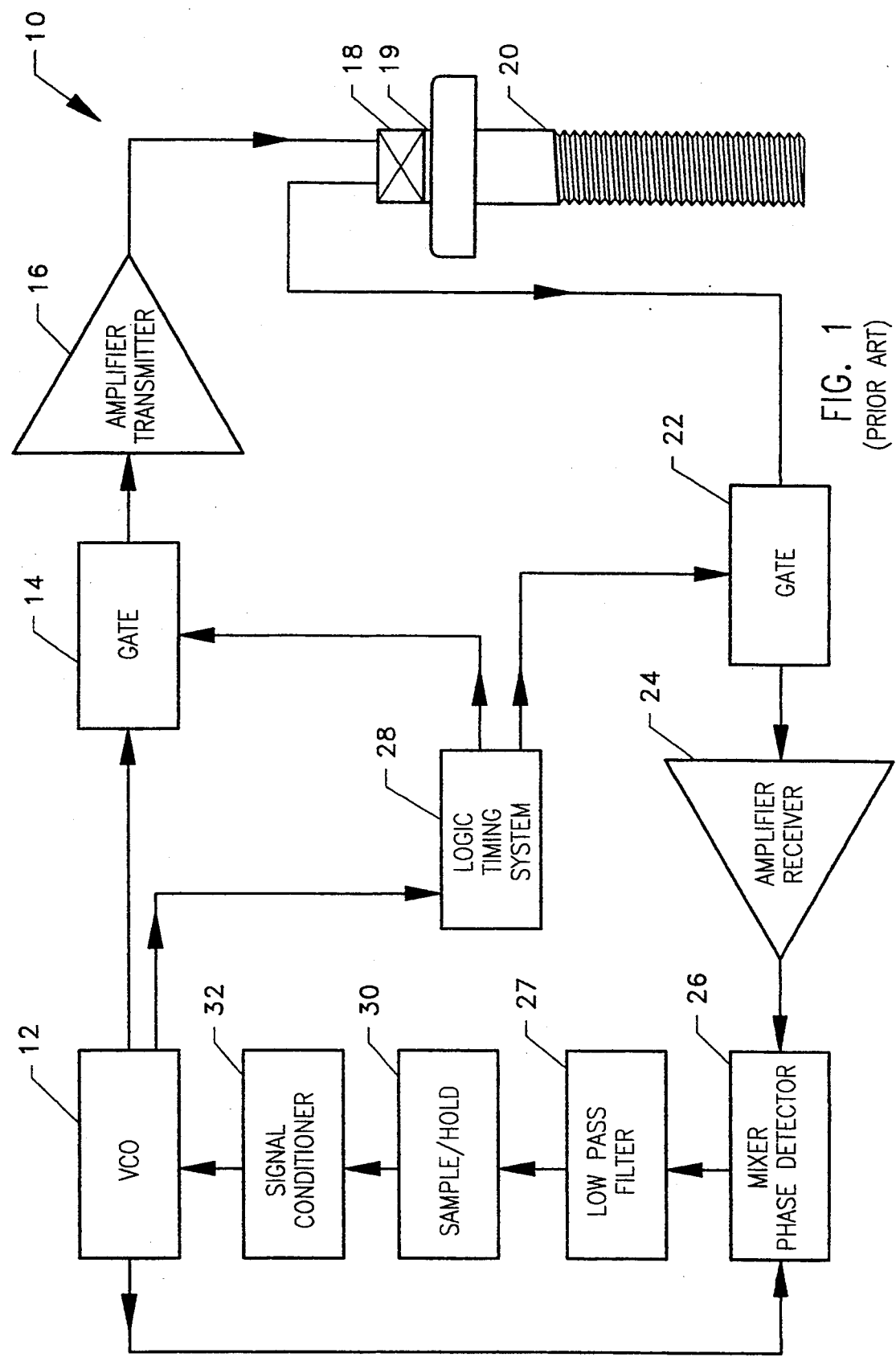
FIG. 1 is a block diagram of a pulsed phase locked loop strain monitor according to the prior art incorporating a low pass filter.

Referring to FIG. 1, a pulse phase locked loop strain monitor or P2L2 10 according to the prior art is schematically shown. The P2L2 is described in greater detail in U.S. Pat. No. 4,363,242 to Heyman, the specification of which is hereby incorporated by reference. The P2L2 measures acoustic phase change and reads out corresponding frequency changes. In general terms, the RF output signal of a voltage controlled oscillator (VCO) 12 is periodically gated by transmitting gate 14 and then amplified and transmitted via amplifier transmitter 16 to an ultrasonic transducer 18. Transducer 18 is affixed to an end of load bearing test material 20 via an appropriate couplant 19 such as water, glycerin, light machine oil, etc. and produces an acoustic tone burst or sound wave pulse which propagates in bearing member 20. The produced acoustic signal may have any appropriate ultrasonic frequency, preferably near the center of the operating frequency bandwidth of the compound resonator formed by the transducer bonded to the load bearing test material. Test material 20 may be a load bearing member such as a bolt or other load bearing component of any geometrical configuration.

The generated tone burst or sound wave pulse is reflected by the far end of test material 20 back to transducer 18 and converted to an electrical signal by the transducer. Transducer 18 in this embodiment both transmits and receives the tone burst; of course, distinct transmitting and receiving transducers can be used to "pitch" and "catch" the tone burst. The signal is gated by sample gate 22, amplified by amplifier receiver 24, and sent to mixer phase detector 26. Mixer phase detector 26 also receives the output of VCO 12 and produces a DC signal proportional to the phase difference between this input and the received transducer signal. This phase difference signal passes through a low pass filter 27 which filters undesired frequencies. Logic timing system 28 controls the gating time of gates 14 and 22 in response to a signal received from VCO 12. Logic timing system 28 also controls the time at which a phase point of the filtered phase difference signal is sampled and held by sample/hold circuit 30. This sampled signal is then appropriately conditioned by signal conditioner 32 and sent to VCO 12 to control the VCO output frequency to maintain this fixed phase difference. The P2L2 locks onto resonant frequencies which correspond to quadrature which represents a phase delay of $2\pi N + \phi_o$, where N is an integer and $\phi_o$ is typically 90°. The value of $\phi_o$ is approximately 0° (zero), in phase (not quadrature) in the modified P2L2 discussed below in reference to FIGS. 3 et seq.

Figure 2:
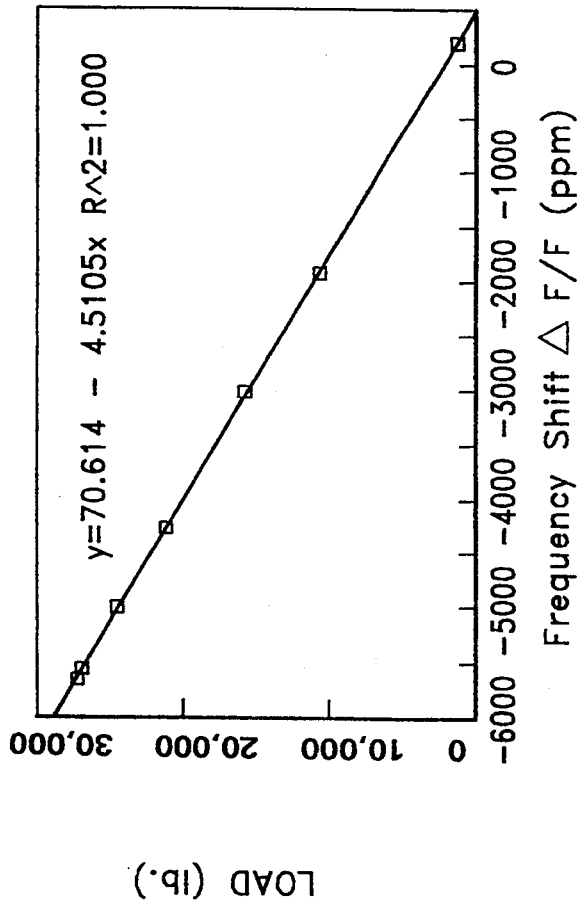
FIG. 2 graphs the load versus frequency shift of a pulsed phase locked loop strain monitor.

Once the frequency F is locked at a particular lock point (described below), any deviation in the propagation length or sound velocity of the test material 20 results in a frequency change $\Delta F$ needed to maintain a fixed phase condition. This frequency change $\Delta F$ is indicated by any conventional means such as a frequency counter providing an electronic readout of the VCO 12 frequency or frequency difference and/or an oscilloscope providing a visual display. Thus, the P2L2 10 measures frequency changes to indicate load changes, i.e., tension or compression, which change the sound velocity and propagation length. This frequency change relationship ($\Delta F/F$) resulting from the load change is the dominant term and is interpreted via a load-member-specific ultrasonic load calibration factor Cl, which is defined in units of Lb/ppm to indicate pounds of load change per parts per million of normalized frequency shift. The factor Cl is determined by obtaining frequency changes resulting from known loads for the particular bearing member and obtaining a polynomial function which represents an acceptable curve fit for the obtained data. For simplicity, a first order linear polynomial is generated and the x-coefficient representing the slope of the curve is expressed as Cl. Then when the load is changed, the normalized frequency shift is multiplied by the Cl factor to determine the load change. See FIG. 2. This function of the P2L2 is discussed in greater detail in the identified related applications, the specifications of which are hereby incorporated by reference.

As stated in the Background section, the low pass filter 27 causes errors in the phase measurement due to the step response of the filter. The mixer output is a voltage that must be filtered. Because the phase voltage is zero until a toneburst is received and upon receipt the mixer output contains both a DC (phase) term and an AC term (2F), the filter has a defined impulse response.

A simple monopole filter has an impulse response $f_{IR}(t)$ that can be expressed as $$f_{IR}(t) = Ae^{-wt} \tag{1}$$

wherein A is the amplitude, t is time, and w is the cutoff frequency expressed in radians.

Let $w = 2\pi(Fp/10)$, wherein F is the operating frequency and P = number of periods required for settling time, i.e., for the filter output to settle to a value having an acceptable error. The time t is equal to P/F. Accordingly, $$F_{(P)} = Ae^{-2\pi(F/10)(P/F)} = Ae^{-2\pi(P/10)}. \tag{2}$$

Since bolt load measurement typically requires one nanosecond accuracy, for F = 5 MHz $$1/220 = e^{-2\pi(P/10)}. \tag{3}$$

Solving for P, $$P = 8.4 \text{ periods.} \tag{4}$$

This means that a toneburst of at least nine periods must be used in order for the filter to have settled to an acceptably correct voltage. In practice an even longer toneburst is required to ensure settling with reasonable confidence. Unfortunately, tonebursts of five to six periods are often needed to evaluate certain loading members, making the filter step response unacceptable.

Figure 3:
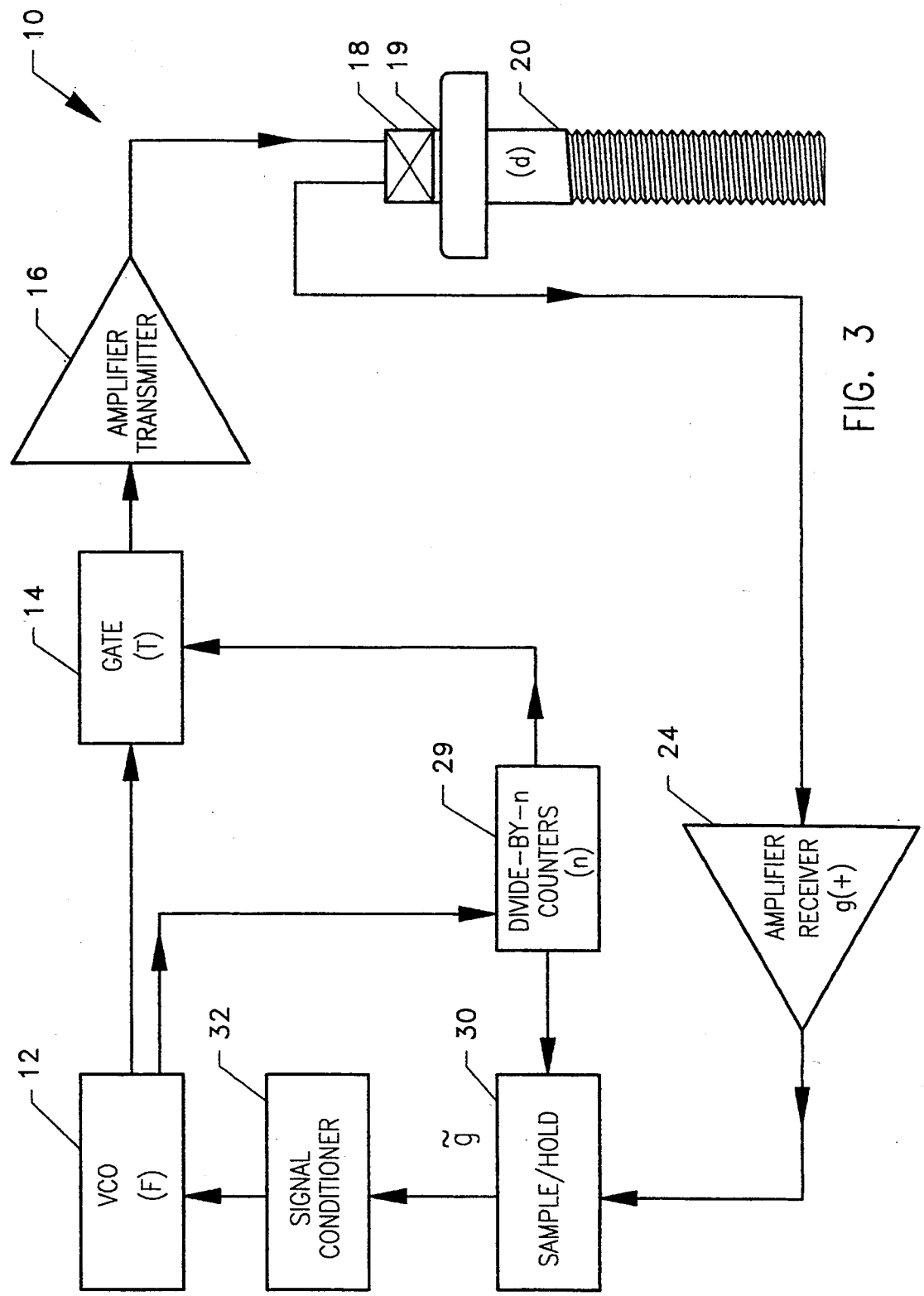
FIG. 3 is a block diagram of a pulsed phase locked loop (P2L2) strain monitor according to the present invention.

Referring now to FIG. 3, an embodiment of the present invention is shown which eliminates the step response problem of the low pass filter. Numbered elements in FIG. 4 have the same configuration and function as like numbered element in FIG. 1. Note that the elements are also identified with variables discussed in the below equations. As seen, the mixer phase detector 26 and low pass filter 27 of FIG. 1 are removed from the P2L2 system 10, as is gate 22. Divide-by-n counters serve as the logic and timing system. Divide-by-n counters 29 control transmitting gate 14 in response to the output frequency F of the VCO 12. The gate 14 is thus opened at a gating frequency of F/h, wherein h is an integer, and the gated output frequency is converted to an acoustic wave transmitted by transducer 18 through bolt 20. The integral number h is set by an operator or by computer 38 shown in FIG. 5.

The computer 38 is preferably programmed to perform the following comparisons and to compute the associated equations based on contemporaneously obtained or previously obtained data. A sample computer code is submitted in accordance with §608.05 of the Manual of Patent Examination and Procedure. The submitted code is used to automatically recertify bolt loads. In addition, the code contains an algorithm which measures the amplitude A of the signal at each sample/hold position n. These measured amplitudes are then used to automatically select an appropriate n. Visual selection of n remains an option, but it has been found to be rarely needed when using the submitted code.

Figure 4:
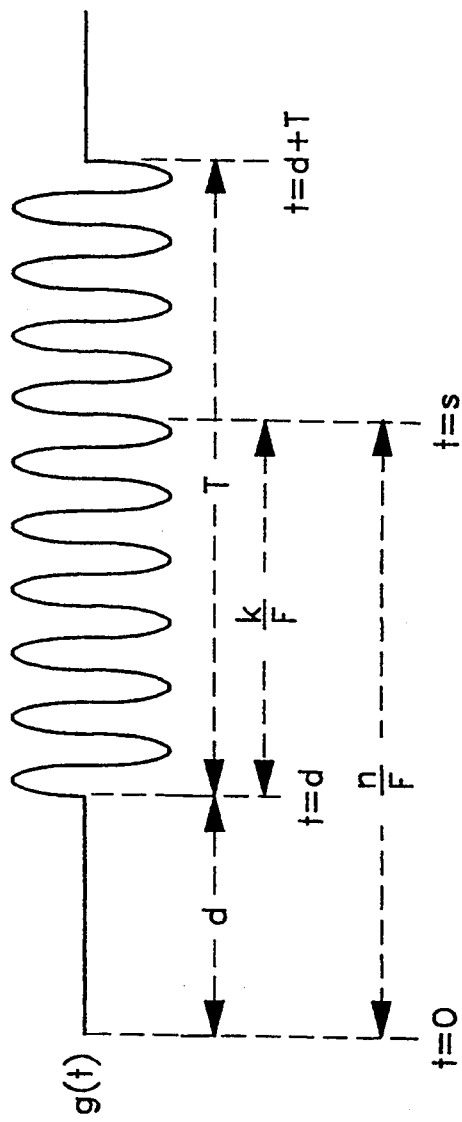
FIG. 4 is a time line representing the time history of a received toneburst employed by the present invention.

Referring to FIGS. 3 and 4, the signal g(t) received by transducer 18 is represented by $$g(t) = A \sin(2\pi F(t-d)) \tag{5}$$

wherein A is the signal amplitude, t is time, and d is the delay time through the bolt, transducer, and interconnecting cables. The toneburst is displayed on an oscilloscope 34 shown in FIG. 5 connected to the VCO 12. A frequency counter 36 is also connected to VCO 12 for displaying F. The received signal is sampled when $$s = \frac{n}{F} \quad (6)$$

wherein n is the sample/hold position set by the operator or the computer in the divide-by-n counters. The time s when the signal is sampled by the sample/hold 30 is thus produced by counting the integral number n of clock periods that follow the beginning of a transmission. This integral number n is set by the operator or computer, counted by the digital counters in the divide-by-n circuitry and remains fixed for a given bolt length, i.e., for a given propagation path in a test material, and operating frequency F. The bolt length must be known only to 0.25" at 5 MHz in order to properly choose s, and hence n, assuming that steel is the material, and that the velocity is well defined. This integral number n is referred to as the sample and gating integer n in the following discussion. This sampling is referred to as synchronous undersampling because the sampling is synchronized to the transmission.

The ideal sampled signal g is thus equation (5) rewritten as t=s, i.e. or $$g = A \sin\left(2\pi F\left(\frac{n}{F} - d\right)\right) \quad (7)$$

or $$g = A \sin 2\pi(n - dF). \quad (8)$$

The feedback in the locked P2L2 circuit causes the VCO to adjust the output frequency F so that g=0 when the P2L2 is in the so-called locked position. Because of this feedback mechanism, only the rising edges of the signal are stable lockpoints, as depicted by the circles LP in FIG. 6. Rewriting equation (8)

$$0 = \sin(2\pi(n-df)) \quad (9)$$

The stable solutions when locked at lockpoint LP on rising edges of the lockpoint regions LR are thus $$2\pi k = 2\pi(n - dF) \quad (10)$$

$$k = n - dF \quad (11)$$

$$d = \frac{n}{F} - \frac{k}{F} \quad (12)$$

wherein k is an unknown. From FIG. 6, k is the number of periods between the arrival of the beginning of the toneburst and the sampling at time s, i.e., it is a characteristic of the lockpoint. Many different lockpoints can have the same k. In general, k is not known and is not an integer except in the ideal case. As detailed below k does not need to be calculated when the P2L2 is locked and the bolt is tightened in the same time frame. In cases where the measurement is interrupted, k is determined with sufficient accuracy to permit the lockpoint to be determined.

Since strain is a relative measurement of the change in length divided by the total length, only the initial pre-loading and the final post-loading locked frequencies need to be known as long as the constant k is the same for each.

From equation (11), $$k = n - (d + \Delta d)(F + \Delta F) \quad (13a)$$

or $$k = n - dF - d\Delta F - F\Delta d - \Delta d\Delta F \quad (13b)$$

wherein $\Delta d$ is the increase in time delay due to the length increase of the bolt due to tensioning, and $\Delta F$ is the increase in frequency to maintain the locked condition g(t)=0. Combining equations (11) and (13b), $$k = k - d\Delta F - F\Delta d - \Delta d\Delta F. \quad (14)$$

The "k" term on each side of the equality is dropped. Since $\Delta d << d$ and $\Delta F << F$, the $\Delta d\Delta F$ is negligible and may also be dropped. Thus, $$d\Delta F = -F\Delta d \quad (15)$$

$$\frac{\Delta F}{F} = -\frac{\Delta d}{d} \quad (16)$$

$$\frac{2(F_2 - F_1)}{F_2 + F_1} = -\frac{\Delta d}{d} \quad (17)$$

where $F_1$ is the initial locked frequency and $F_2$ is the final locked frequency of the P2L2.

The load determination is often interrupted by removing the transducer from the loading member, e.g., a bolt. For example, it is desirable to periodically measure the load on a bearing member to assess its current status without having a transducer coupled to the bearing member in between measurements.

A method is accordingly needed to guarantee that k has not changed when obtaining the post-interruption $\Delta F$ to determine the load. Recalling equation (11), k=n−dF. Since n is set explicitly by the operator or computer and F is measured explicitly by, e.g., the frequency counter 36, two unknowns are present. Accordingly, a new relationship is defined by advancing n by 1 and increasing the frequency F by F/n such that a new variable k' is defined by $$k' = (n+1) - d(F + F/n) \quad (18)$$

$$k' = n - dF + 1 - dF/n \quad (19)$$

Rewriting equation (11) as dF=n−k and substituting into equation (14), $$k' = n - (n-k) + 1 - (n-k)/n \quad (20)$$

$$k' = k + k/n. \quad (21)$$

It is known experimentally that for most bolts $k \approx 10$ when $n \approx 100$. To meet the condition that k/n<1/10, the total delay through the bolt must be ten times the toneburst length. In general, toneburst lengths are kept as short as possible. The new k' is thus within one tenth of a cycle of k. When the P2L2 is locked, the frequency will be adjusted as is known so that k'=k. Accordingly, $$k = n_1 - dF_1 \quad (22)$$

$$k' = n_2 - dF_2 \quad (23)$$

$$n_1 - dF_1 = n_2 - dF_2 \qquad (24)$$

$$n_1 - n_2 = d(F_1 - F_2) \qquad (25)$$

$$d = \frac{n_1 - n_2}{F_1 - F_2} \qquad (26)$$

Combining equations (26) and (22)

$$k = n_1 - \frac{n_1 - n_2}{F_1 - F_2} F_1 \qquad (27)$$

$$k = \frac{F_1 n_2 - F_2 n_1}{F_1 - F_2} \qquad (28)$$

wherein $F_1$ is the initial operating frequency, $F_2$ is the subsequent operating frequency equal to $F_1 + (F_1/n_1)$, $n_1$ is the initial value of n, and $n_2$ is $n_1 + 1$.

The method is first performed prior to the subject interruption. Note that the transducer and/or the P2L2 need not be of the type disclosed in the present invention, although the disclosed design results in good measurements due to the improved response. Specifically, the sample/hold is set at $n_1$ and the P2L2 is locked at $F_1$. The value $n_1$ is chosen so that it falls within the toneburst received. Currently, this is done visually. The P2L2 is then unlocked, the sample/hold adjusted to $n_2 = n_1 + 1$, and then the P2L2 is relocked so that $F_2 = F_1 + F_1/n_1$. The value "k" is then determined via equation (28) and stored in computer 38. After the subject interruption, the transducer is coupled to the bolt and the P2L2. The transducer and P2L2 used after the interruption do not need to be the same as those used before the interruption. If they are not, both transducers and instruments must be carefully calibrated. Once the transducer is coupled to the loading member, the same k value must be obtained to permit accurate determination of the post-interruption $\Delta F$. The sample/hold is set at $n_x$, wherein x normally is initially 1, i.e., $n_x = n_1$. The foregoing procedure is repeated and $k_x$ is obtained via equation (28) and compared to the stored value k. Specifically, $n_x$ is advanced by one such that $n_{x+1} = n_x + 1$ and the P2L2 is locked so that the output and reference signals have a frequency $F_{x+1} = F_x + F_x/n_{x+1}$. The value $k_x$ is computed to be $(F_x n_{x+1} - F_{x+1} n_x)/(F_x - F_{x+1})$ per equation (28) and compared to the stored value for k. This advancement of n need not be reproduced. The measurement value of $k_x$ will tell the operator how far and in what direction $k_x$ is from the correct k. Once INT($k_x$) approximates INT(k), the load is calculated in the described manner wherein $\Delta F = F_x - F_1$. INT(k)$_x$ is considered to approximate INT(k) when $/k - k_x/ < 0.5$. If this inequality is not met, the difference $k - k_x$ gives the number of lockpoint adjustments necessary to obtain the desired approximation. The calibration factor Cl is stored in computer 38 and displayed via a printer and/or plotter 40, shown in FIG. 5.

Note that the definitions of d and k in equations (26) and (28) involve differences in the denominator which significantly reduce the precision of the measurement. However, the resulting accuracy is more than sufficient to properly determine k within a required few percent.

Figure 6:
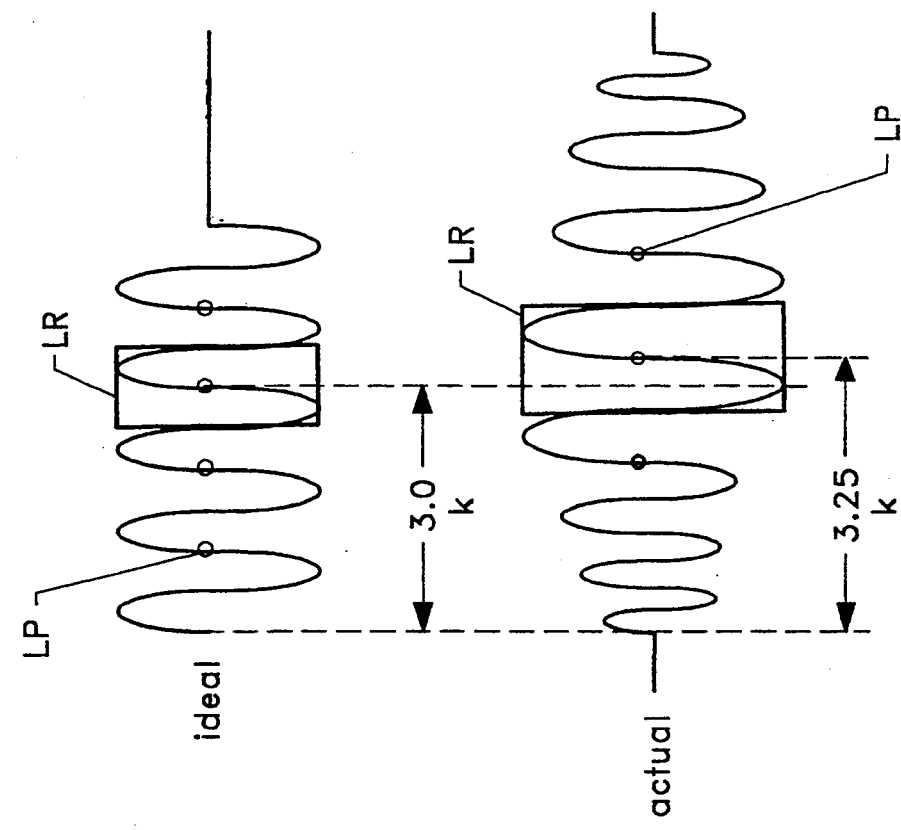
FIG. 6 graphs an ideal and actual toneburst.
Figure 7:
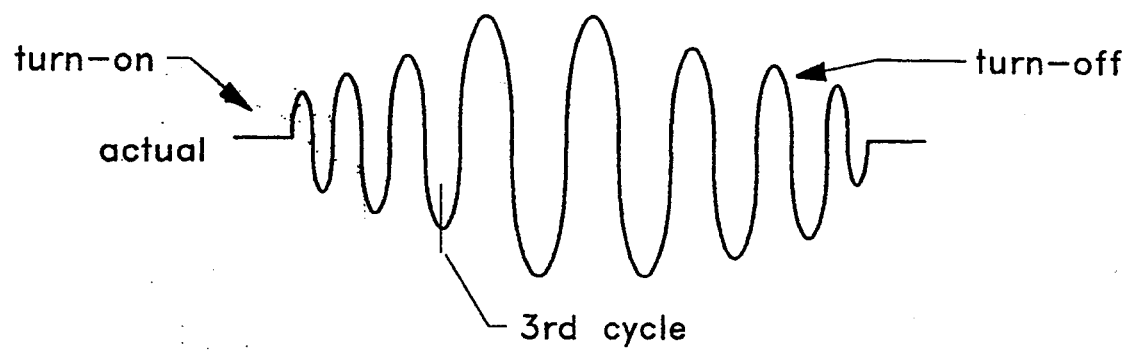
FIG. 7 graphs the effects of linear distortion of an actual toneburst as displayed in FIG. 6.

Calibration of the transducer is also important for improving the accuracy of the P2L2 system. The prior discussion and equations employ an ideal toneburst which cannot be reproduced in a real electronic and/or acoustic system, as represented by FIG. 6. Specifically, the transducer and associated electronics cause linear distortions in the signal which cause the initial turn-on portion of the signal and final turn-off portion of the signal to be at a different frequency than the ideal toneburst, wherein in some cases the turn-on portion frequency gradually increases to the ideal toneburst frequency and the turn-off portion frequency gradually decreases from the ideal toneburst frequency, as shown in FIG. 7. The direction of frequency change will be different for different transducers and driving frequencies. The distortion effects are a characteristic solely of the transducer when the same P2L2 is used.

The theory of linear systems guarantees that if the toneburst is long enough, the signal will eventually reach the frequency of the toneburst. With a broadband transducer having a bandwidth equal to its frequency, the signal will usually be at the toneburst frequency within three cycles. At this time, the previously discussed equations will apply except that k is no longer an integer. As shown in FIG. 6, k will now comprise an integral and fractional part. This fractional part, 0.25 in FIG. 5, changes with frequency. Accordingly, the effect of frequency on k must be measured to permit absolute measurements and the comparison of measurements taken by different transducers.

The following discussion assumes a "constant" path length. Such a constant length assumes only minor fluctuations in the length from, e.g., temperature and/or load changes. For the purposes of this application, a path length for a bolt is acceptably "constant" if the time of flight of an acoustic wave is within 100 picoseconds. Acceptable ranges are dependent on the particular bearing member.

Equation (9) for the locked condition ignores the effect of the transducer on the signal. To compensate for the transducer effect, for generality it is assumed that the phase shift $\beta$ through the transducer as a function of frequency is some arbitrary polynomial $$2\pi\beta(F) = 2\pi(e_0 + e_1 F + e_2 F^2 + e_3 F^3 + \ldots \qquad (29)$$

Combining equation (29) with equation (9) to take transducer effects into account results in $$0 = \sin\,(2\pi(n - dF) - 2\pi(e_0 + e_1 F + e_2 F^2 + e_3 F^3 + \ldots \\ )) \qquad (30)$$

$$0 = \sin\,(2\pi(n - (d + e_1)F - e_0 - e_2 F^2 - e_3 F^3 + \ldots\,)). \qquad (31)$$

The term $e_1$ is a static error in the delay measurement. Thus, if we have a path of constant but unknown length, all of the coefficients in equation (31) can be determined except $e_1$.

For stable lockpoints, $$2\pi k = 2\pi(n - (d + e_1)F - e_0 - e_2 F^2 - e_3 F^3 + \ldots\,). \qquad (32)$$

Solving for part of the polynominial $$e_0 + e_2 F^2 + e_3 F^3 + \ldots = n - (d + e_1)F - k \qquad (33)$$

Defining $\beta'(F)$ as $\beta(F)$ minus the $e_1$ term, $$\beta'(F) = n - (d + e_1)F - k \qquad (34)$$

To measure $\beta'(F)$, a set of measurements is required at different frequencies where k is held constant and both F and n are known. The value k is kept constant as discussed before with respect to interrupted measurements (equation (13) et seq.). Using this method, if the P2L2 is at a lockpoint where the sample/hold position is $n_P$ and the frequency is $F_P$, then the next successive lockpoint P+1 is near $$n_{P+1} = n_P + 1 \tag{35}$$

and $$F_{P+1} = F_P + F_P/n_P. \tag{36}$$

The sample/hold is adjusted to $n_{P+1}$ and the P2L2 relocked so that VCO will be adjusted to $F_{P+1}$. Repeating the procedure N times produces an array of points $$P = 1, N:(n_P, F_P) \tag{37}$$

The integer N is the number of successive one increment advancements of the gating and sampling integer n required to achieve acceptable accuracy of the following approximation. Following the established nomenclature, $F_N$ is the frequency of the output and reference signals at $n_N$ when the P2L2 is locked.

The value $(d+e_1)$ is approximated using equation (26) to result in $$d + e_1 = \frac{n_1 - n_N}{F_1 - F_N} \tag{38}$$

This approximation will have a large error because it is a difference measurement. The error is corrected by employing a standard reference material of sufficient accuracy, e.g., 100 ps as described previously. The accuracy obtained will probably be limited by the rebond accuracy of subsequent transducers.

Referring once again to equation (28), k is computed and rounded to the nearest integer $$k = INT\left[\frac{F_1 n_N - F_N n_1}{F_1 - F_N}\right] \tag{39}$$

Referring to equation (34), all of the variables are now defined. Specifically, n is established by the sample/hole setting, F by the frequency counter, $(d+e_1)$ by equation (38), and k by equation (34). $\beta'(F)$ can now be defined for each frequency $F_P$, i.e.

$$\beta'(F_P) = n_P - (d-e_1)F_P - K \tag{40}$$

Rewriting equation (40) yields $$\beta'(F_P) = n_P - \frac{(n_1 - n_N)}{(F_1 - F_N)} F_P - INT\left[\frac{F_1 n_N - F_N n_1}{F_1 - F_N}\right] \tag{41}$$

Figure 8:
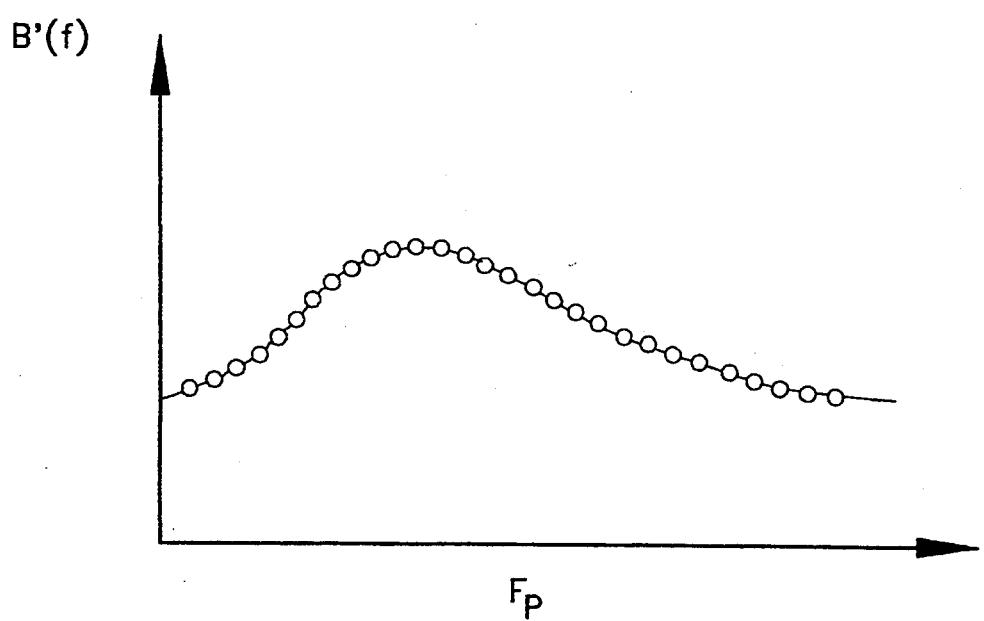
FIG. 8 graphs a transducer specific calibration curve generated according to the present invention.

A transducer specific calibration curve of $\beta'(F)$ versus F is shown in FIG. 8. If the transducer is well behaved, $\beta'(F)$ will be a smooth curve. In the case of a smooth curve, linear interpolation can be used to approximate the transducer-specific $\beta'(F)$ for all values of F. All Harrisonic transducers tested have behaved well. This behavior is possibly because of a tuned inductor built into the transducer.

Figure 5:
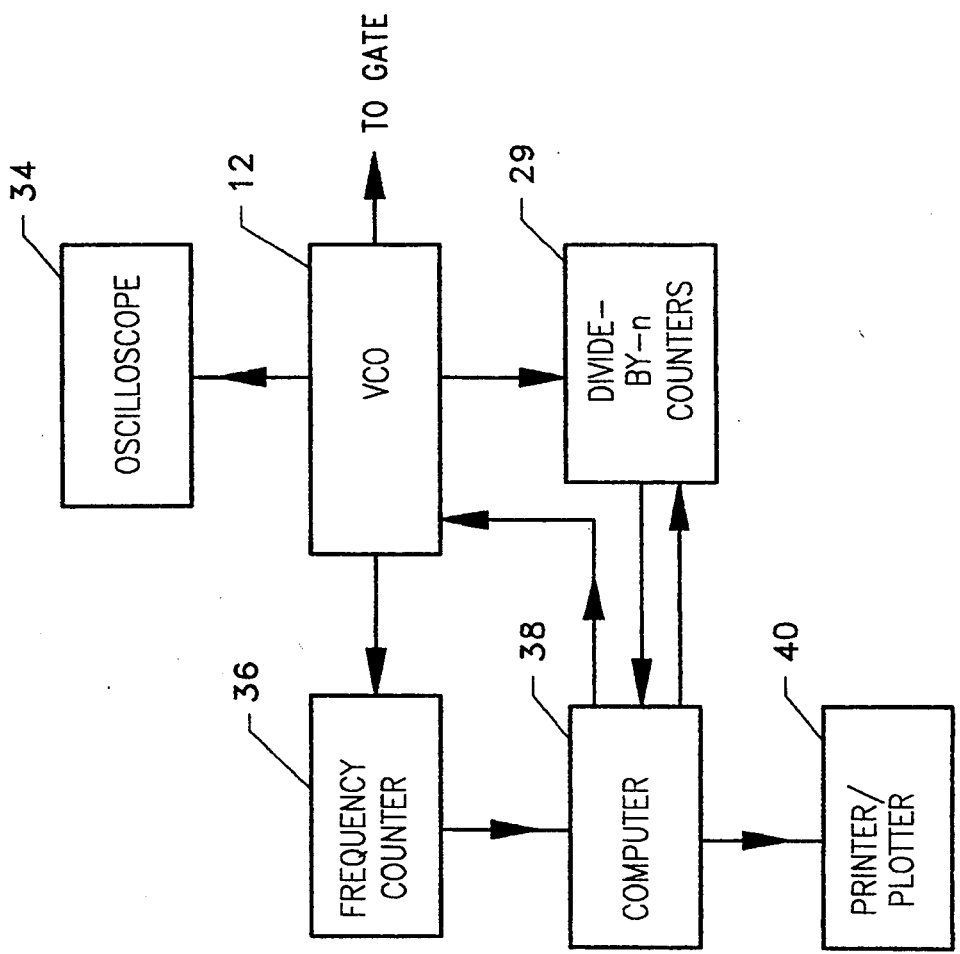
FIG. 5 is a schematic diagram of monitoring and control equipment according to the present invention used with the P2L2 strain monitor of FIG. 3.

Both the frequency F and the sample hold/setting n may be input into an appropriate computer 38 as shown in FIG. 5. Each specific $F_P$ and $n_P$ is input and $\beta'(F_P)$ is calculated therefrom per equation (35). After N inputs and calculations, $\beta'(F)$ is defined with sufficient accuracy to generate a calibration curve. A calibration curve is generated for each transducer. Once a calibration curve is obtained for a specific transducer, the transducer transmission and reception are calibrated by obtaining the value of $\beta'$ for the particular operating frequency $F_P$ of that transducer and subtracting this phase shift $2\pi\beta'(F_P)$ from the frequency. In pitch/catch mode, the transducer pair would need to be calibrated. That would be the only change from the single transducer embodiment described. The calibration curve is often a straight horizontal line, representing a transducer-specific calibration factor applicable to the entire frequency band of the transducer.

Once $\beta'(f)$ is determined, eq. (34) is rewritten in terms of k to be $$k = (n - (d+e_1)F - \beta'(F)). \tag{42}$$

Solving for $d+e_1$, which designates the time of flight of the acoustic toneburst through the sample and transducer $$\frac{n - k - \beta'(F)}{F} = d + e_1. \tag{43}$$

Now, however, k is strictly an integer and must be properly rounded. The computation for k on a calibrated transducer should also be modified.

Solving for k at two sample/hold positions and associated frequencies $$k = n_1 - (d+e_1)F_1 - \beta'(F_1) \tag{44a}$$

$$k = n_2 - (d+e_1)F_2 - \beta'(F_2). \tag{44b}$$

Combining eqs. (44a) and (44b) yields $$k = \frac{F_1[n_2 - \beta'(F_2)] - F_2[n_1 - \beta'(F_1)]}{F_1 - F_2}, \tag{45}$$

which relates to eq. (28) with calibration. Calibration allows the time-of-flight, $d+e_1$, to be accurately calculated from the frequency and sample/hold position. Note that since this calibration assumed a constant but unknown path length, the static error, $e_1$, remains. This error could easily be eliminated if a standard pathlength as defined before were available.

Figure 9:
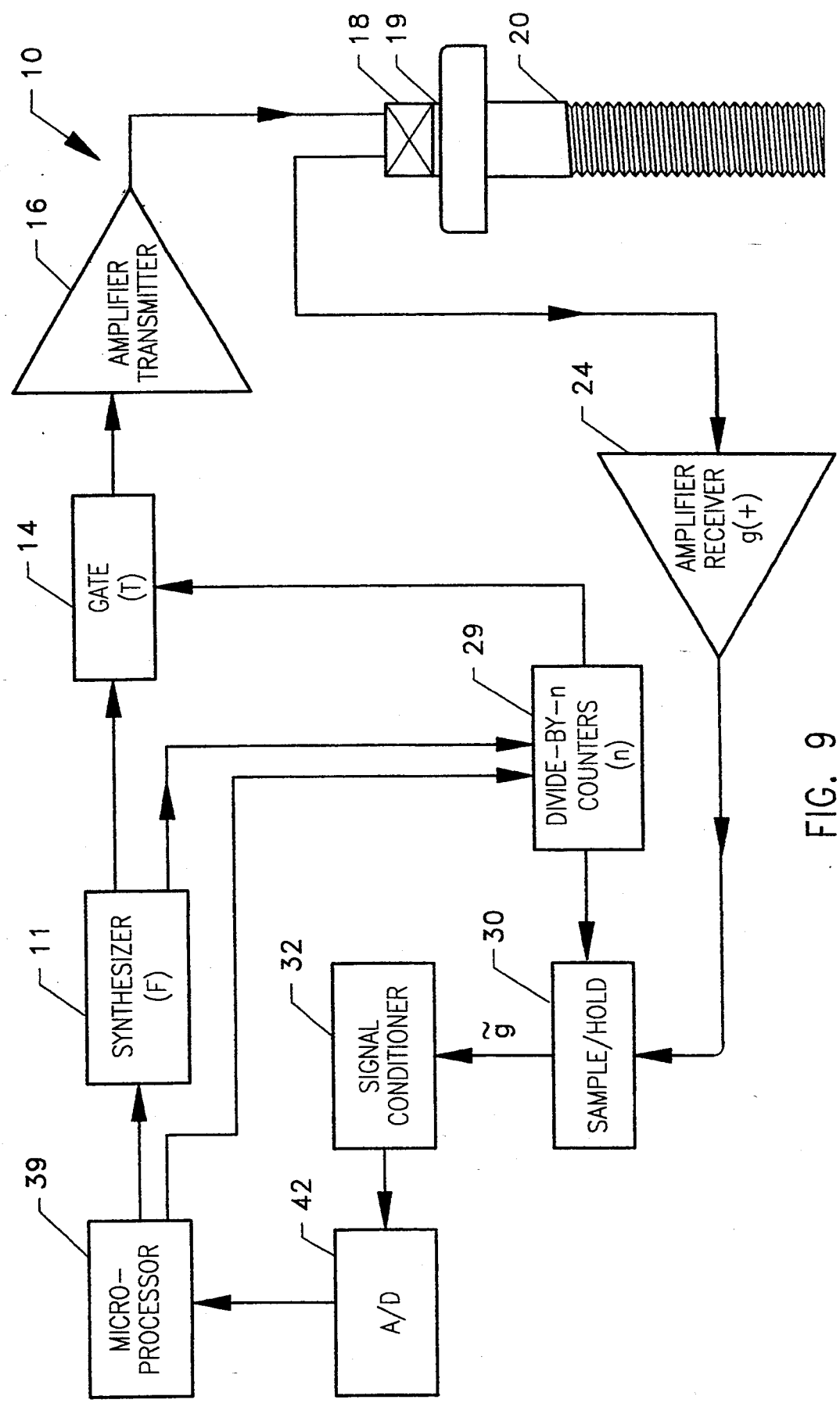
FIG. 9 is a block diagram of another embodiment of the present invention.

In another embodiment of the present invention, shown in FIG. 9, the VCO 12 is replaced with a digitally controlled direct digital synthesizer 11 such as STEL 1375 available from Stanford Telecomm. The analog phase signal of Eq. (5) generated by sample/hold 30 is converted to a 16-bit digital word by an A/D converter 42 such as Model MN6400 commercially available from Micro Networks. This digitized signal is passed through a microprocessor 39 or computer 38 (see FIG. 5) which closes the control loop. Use of digital frequency synthesis increases the stability of the P2L2 system and eliminates the need for frequency measurement by, e.g., the frequency counter 36 of FIG. 5. Use of a microprocessor or computer to close the control loop permits the control laws of the system to be optimized for each measurement. Computer control of the sample and hold position by controlling divide-by-n counters 29 and computer control of the frequency by controlling the synthesizer 11 permits complete automation of the system. All of the foregoing settings and equations are straightforwardly programmed into the controlling computer.

The transducers could also be calibrated for temperature induced deviations, as discussed in the related co-pending applications.

Many substitutions, modifications, and improvements will be apparent to the skilled artisan without departing from the spirit and scope of the present invention as described herein or defined in the following claims.

```
2 DIM D % (6)
4 DIM V(1000), DF(500)
5 DIM Y(2000),F(500)
6 DIM FL(500),HN(500),SP(500)
7 DIM LB(500),FLB(500)
  GS %=4
9 DIM X1(1000)
10 DEF SEG=&H8000
11 OCLB=94
20 BLOAD "pdma.bin",0
30 PDMA=0
40 MD %=0
60 FLAG %=0
70 D % (0)=&H300
80 D % (1)=3
90 D % (2)=5
100 CALL PDMA (MD %,D % (0),FLAG %)
110 IF FLAG<>0 THEN PRINT "error number";-FLAG %:STOP
120 GOSUB 3000
130 GOSUB 3100
200 PRINT "1-SET UP AND CALIBRATE NEW BOLT"
210 PRINT "2-READ OLD BOLT FILE AND MEASURE BOLT"
228 PRINT "3-SET NEW ZERO LOAD FREQUENCY"
230 PRINT "4-TRACK LOAD"
232 PRINT "5-SAVE RE-ZEROED BOLT"
239 PRINT
240 INPUT "CHOOSE 1, 2, 3, 4, 5, 6, 7, 8, 9";C
250 ON C GOSUB 4300,4400,1200,4000,2700
260 GOTO 200
300' SET FREQUENCY ROUTINE
302 CLS
305 INPUT "ENTER FREQUENCY, IN Hz";F0
310 DPHI#=85.8993*F0
320 X#=DPHI#
330 B3%=INT(X#/16777216#)
340 X#=X#-B3% *16777216#
350 B2%=INT(X#/65536!)
360 X#=X#-B2% *65536!
370 B1%=INT(X#/256)
380 X#=X#-B1% *256
390 B0%=INT(X#)
400 A%=176:B%=B0%
410 GOSUB 1000
415 A%=177:B%=B1%
420 GOSUB 1000
430 A%=178:B%=B2%
440 GOSUB 1000
450 A%=179:B%=B3%
455 GOSUB 1000
460 GOSUB 1300
470 RETURN
480' ACCEPT NEW TRANSMIT WIDTH
481 INPUT "ENTER TRANSMIT WIDTH (INTEGER BETWEEN 0,255)";GA %
485 A%=129:B%=GA %
487 GOSUB 1000
490 A%=255
492 GOSUB 1000
495 RETURN
500' READ AND DISPLAY RETURN ECHO AMPLITUDES
510 GOSUB 900
520 GOSUB 3500
530 RETURN
550' READ LOCKPOINTS AND DETERMINE K
560 GOSUB 2200
570 GOSUB 700
572 F0=FL(1):OC=HN(1)-GS %
574 GOSUB 310
576 GOSUB 3320
580 RETURN
600' READ AND CORRECT K
605 GOSUB 2200
610 GOSUB 700
615 DK=SGN(KF-KLB)*INT(ABS(KF-KLB)+0.5)
620 IF DK=0 THEN 660
625 OC=HN(1)-GS %
630 F0=FL(1)+FL(1)*DK/HN(1)
635 GOSUB 3320
640 GOSUB 310
650 GOTO 605
660 OC=HN(1)-GS %
665 F0=FL(1)
670 GOSUB 3320
675 GOSUB 310
680 'PRINT OC,OCLB,F0,F0LB
690 RETURN
700' COMPUTE K
710   KF=(FL(1)*HN(NL)-FL(NL)*HN(1))/(FL(1)-FL(NL))
715 'PRINT "MEASURED K IS";KF
730 TF=(NL-1)/(FL(NL)-FL(1))
735 'PRINT "TIME OF FLIGHT IS";TF;'SECONDS"
736 LD=A+B*2*(F0LB-FL(1))/(F0LB+FL(1))
738 'PRINT "THE CURRENT LOAD IS";LD
740 RETURN
800 'SET SAMPLE HOLD (OCLB)
810 INPUT "ENTER DESIRED SAMPLING AREA";OCLB
820 RETURN
850' CALIBRATE BOLT AND GENERATE CURVE FIT
860 GOSUB 2000
870 GOSUB 3700
880 RETURN
900' READ ECHO AMPLITUDES
901 CLS
902 LOCATE 10,5
903 NR=3
905 PRINT "READING 80 VALUES";
907 WN=INT(10+OC*11000/F0)
910 FOR X=1 TO 80
915 OC=X+OCLB-40
917 GOSUB 3320
920 GOSUB 1700
921 FOR J=1 TO WN:NEXT J
922 LY=0
925 K=0
930 FOR K=2 TO NR
940 LY=LY+V(K)
945 NEXT K
```

```
950 LY=LY/NR
955 F1=F0
957 F0=F0+F0/4/(OC+9)
958 GOSUB 310
960 GOSUB 1700
691 FOR J=1 TO WN:NEXT J
962 LX=0
963 K=0
964 FOR K=2 TO NR
965 LX=LX+V(K)
966 NEXT K
967 LX=LX/NR
970 F0=F1
975 GOSUB 310
976 LOCATE 10,27
977 Y(X)=SQR(LX*LX+LY*LY)
978 X1(X)=OC
979 PRINT X
980 NEXT X
985 XMAX=80
990 RETURN
1000' WRITE B % TO ADDRESS A %
1010 MD %=4
1020' SET ADDRESS
1030 D % (0)=A %
1040 D % (1)=0
1050 CALL PDMA (MD %,D % (0),FLAG %)
1060' SET DATA
1070 D % (0)=B %
1080 D % (1)=1
1090 CALL PDMA (MD %,D % (0),FLAG %)
1100' PULSE WRITE LINE LOW
1110 MD %=6
1120 D % (0)=0
1130 D % (1)=0
1140 D % (2)=1
1150 CALL PDMA (MD %,D % (0),FLAG %)
1160 D % (0)=1
1170 CALL PDMA (MD %,D % (0),FLAG %)
1180 RETURN
1200' SET NEW ZERO LOAD FREQUENCY
1205 CLS
1210 GOSUB 600
1220 F0LB=FL(1)
1225 CLS
1230 FLB(1)=F0LB
1240 RETURN
1300' PULSE FRLD HIGH (AUX 2)
1310 MD %=6
1320 D % (0)=1
1330 D % (1)=1
1340 D % (2)=1
1350 CALL PDMA (MD %,D % (0),FLAG %)
1360 D % (1)=0
1370 CALL PDMA (MD %,D % (0),FLAG %)
1380 RETURN
1500 PO %=PO %+PI %
1510 IF PO %>=4096 THEN PO %=PO %-4096
1520 IF PO %<0 THEN PO %=PO %+4096
1530 P1%=INT(PO %/16)
1540 P2%=16*INT(PO %-P1%*16)
1550 A %=185:B %=P1%
1560 GOSUB 1000
1570 A %=184:B %=P2%
1580 GOSUB 1000
1590 GOSUB 1300
1592 A %=255
1593 GOSUB 1000
1600 RETURN
1700' READ A/D CONVERTER
1710' N-POINTS STORED IN V(K)
1712 A %=255:B %=255
1713 GOSUB 1000
1720 MD %=1
1730 D % (0)=NR
1740 D % (1)=1
1750 D % (2)=0
1760 D % (3)=0
1770 D % (4)=0
1780 D % (5)=&H5000
1790 D % (6)=0
1800 CALL PDMA (MD %,D % (0),FLAG %)
1810 MD %=2
1820 CALL PDMA (MD %,D % (0),FLAG %)
1830 IF (D % (1)-D % (0))<0 THEN 1820
1835 DEF SEG=&H5000
1840 FOR I=0 TO NR-1
1850    V(I+1)=PEEK(2*I)+256*PEEK(2*I+1)-32768!+DE
1860 NEXT I
1870 DEF SEG=&H8000
1880 RETURN
2000' TRACK AND CALIBRATE ROUTINE
2005 NR=50
2010 F0=FL(1)
2015 IL=0
2020 OC=HN(1)-GS %
2030 GOSUB 310
2040 GOSUB 3320
2050 CLS
2055 LOCATE 4,4
2056 PRINT "FREQUENCY", "TIME (ns)";
2057 LOCATE 7,4
2058 PRINT "LOAD","FREQUENCY","TIME (ns)";
2060 GOSUB 2500
2070 F0=F0-VO/M/85.8993
2075 TOF=INT(1E+10*(OC+GS %- KF)/F0)/10
2080 GOSUB 310
2090 LOCATE 5,4
2100 PRINT INT(F0),TOF;
2105 N$=INKEY$
2110 IF N$="F" THEN CLS:RETURN
2120 IF N$="" THEN GOSUB 2140
2124 LOCATE 1,4
2125 IF IL=16 THEN CLS:RETURN
2126 PRINT "PRESS SPACE BAR TO ENTER LOAD, 'F' END CALIBRATION"
2130 GOTO 2060
2140 LOCATE 1,4
2142 PRINT"";
2143 LOCATE 1,4
2145 IL=IL+1
2150 INPUT "CURRENT LOAD";LB(IL)
2160 FLB(IL)=F0
2170 LOCATE IL+7,4
2180 PRINT LB(IL),FLB(IL),TOF;
2190 RETURN
2200' LOCKPOINT SPACING
2210 NR=30
2215 NL=INT((OC+GS %)/50+0.5)
2216 NJ=0
2220 DF#=DPHI#/(54*OC)
2230 GOSUB 2450
2240 GOSUB 2400
2242 NJ=NJ+1
```

```
2243 FL(NJ)=DPHI#/85.8993
2244 HN(NJ)=OC+GS %
2245 DPHI#=DPHI#+DPHI#/(OC+GS %-KF)
2250 OC=OC+1
2260 GOSUB 3320
2270 GOSUB 320
2275 LOCATE 10,30
2290 PRINT NL-NJ; "LOCKPOINTS LEFT TO READ"
2295 IF NJ→NL THEN RETURN
2300 GOTO 2240
2400' LOCATE ZERO CROSSING
2405 GOSUB 2500
2407 IF ABS(VO)<15 THEN RETURN
2410 DPHI#=DPHI#-INT(VO/M)
2415 GOSUB 320
2420 GOTO 2405
2450' LOCATE ZERO RETURN SLOPE IN M
2455 GOSUB 2500
2457 VI=VO
2458 DF#=DF#*SGN(VO)
2460 DPHI#=DPHI#+DF#
2465 GOSUB 320
2470 GOSUB 2500
2475 IF SGN(VO)><SGN(VI) THEN M=1.41*(VO-VI)/DF#:RETURN
2480 VI=VO
2490 GOTO 2460
2500' READ AND AVERAGE VOLTAGE
2501 FOR J=1 TO 100:NEXT J
2502 GOSUB 1700
2505 VO=0
2510 FOR K=6 TO NR
2520 VO=VO+V(K)
2530 NEXT K
2540 VO=VO/(NR-6)
2550 RETURN
2600' set offset null
2610 DE=0
2620 NR=200
2630 GOSUB 1700
2640 FOR K=1 TO NR
2650 DE=DE+V(K)
2660 NEXT K
2670 DE=-DE/NR
2680 RETURN
2700' WRITE DATA TO DISK
2710 INPUT "BOLT FILE TO WRITE";N$
2715 N$=N$+".BLT"
2720 OPEN N$ FOR OUTPUT AS #2
2740 PRINT#2,FLB(1),OC,KF,GA %,RR %
2750 PRINT#2, A,B,R2
2760 CLOSE #2
2770 RETURN
2800' READ DATA FROM DISK
2805 SHELL("DIR *.BLT>JNK")
20806 PEN "JNK" FOR INPUT AS #2
2808 INPUT #2,F$
2809 PRINT F$
2810 IF EOF(2) THEN 2815
2811 GOTO 2808
2815 CLOSE #2
2817 INPUT "BOLT FILE TO LOAD";N$
2819 N$=N$+".BLT"
2820 OPEN N$ FOR INPUT AS #1
2830 INPUT #1, FOLB,OCLB,KLB,GALB,RR %
2835 INPUT #1, A,B,R2
2837 GOSUB 3220
2838 GOSUB 3220
2840 F0=FOLB
2845 GOSUB 310
2850 OC=OCLB
2860 GOSUB 3320
28790 GA %=GALB
2875 GOSUB 485
2876 CLOSE #1
2880 RETURN
3000' RESET OSCILLATORS
3010 MD %=4
3020' SET ADDRESS
3030 D % (0)=176
3040 D % (1)=0
3045 CALL PDMA (MD %,D % (0),FLAG %)
3050 ' PULSE RESET LOW'
3055 MD %=6
3060 D % (0)=1
3065 D % (1)=0
3070 D % (2)=0
3075 CALL PDMA (MD %,D % (0),FLAG %)
3080 MD %=6
3095 D % (2)=1
3096 CALL PDMA (MD %,D % (0),FLAG %)
3097 A %=255
3098 GOSUB 1000
3099 RETURN
3100' RESET COUNTERS
3110 A %=128
3120 GOSUB 1000
3197 A %=255
3198 GOSUB 1000
3199 RETURN
3200' SET REP RATE
3205' RINT "CURRENT DIVISOR=";RR
3210 INPUT "REP RATE 0-255 ";RR %
3220' M %=INT(RR/256)
3230' L %=INT(RR-RM %)
3240 A %=132: B %=RR %
3250 GOSUB 1000
3260'%=113: B %=RM %
3270' OSUB 1000
3280 A %=255
3290 GOSUB 1000
3295 RETURN
3300 REM SET OFFSET
3310 PRINT "CURRENT OFFSET";OC
3315 INPUT "OFFSET COUNT";OC
3320 RM %=INT(OC/256)
3330 RL %=INT(OC-RM % *256)
3340 A %=130: B %=RL %
3350 GOSUB 1000
3360 A %=134:B %=RM %
3370 GOSUB 1000
3380 A %=255
3390 GOSUB 1000
3395 GOSUB 3100
3400 RETURN
3500' PLOTTING ROUTINE
3510 SHP=0
3520' FIND MAX Y
3525 CLS
3530 YMAX=Y(1)
3535 FOR I=1 TO XMAX
3540 IF Y(I)>YMAX THEN YMAX=Y(I)
3545 NEXT I
3547 FOR I=1 TO XMAX
```

```
3549 IF Y(I)>YMAX/2 THEN OC=XI(I+INT(GA
     %/2)+1):GOTO 3553
3550 NEXT I
3553 XDIS=0
3554 CLS
3565 FOR I=1 TO 80
3566 IF I+XDIS>XMAX THEN GOTO 3630
3567 IF OC=X1(I+XDIS) THEN A1$="X" ELSE
     A1$=CHR$(1)
3570 YV=INT(18*Y(I+XDIS)/YMAX)
3575 FOR J=0 TO YV
ROW=19-J
3585 LOCATE ROW,I
3590 PRINT A1$;
3595 NEXT J
3596 ZD=X1(I+XDIS)
3597 N$=STR$(ZD)
3598 XLEN=LEN(N$)-1
3600 FOR J=1 TO XLEN
3605 B1$=MID$(N$,J+1,1)
3610 ROW=19+J
3615 LOCATE ROW,I
3620 PRINT B1$;
3625 NEXT J
3630 NEXT I
3632 XDIS=XDIS+40
3633 IF XDIS+40>XMAX THEN XDIS=0
3635 LOCATE 2,1
3636 PRINT "MAXIMUM IS";INT(YMAX);
3638 LOCATE 1,1
3640 INPUT"ENTER NEW S/H VALUE, 'N' FOR
     MORE DATA, OR PRESS <CR> TO ACCEPT
     VALUE",SH$
3641 SHP=VAL(SH$)
3643 IF SHP>0 THEN 3660
3645 IF SH$="" THEN GOTO 3670
3650 IF SH$="N" THEN GOTO 3554
3660 OC=SHP
3670 GOSUB 3320
3675 CLS
3680 RETURN
3700' LINEAR CURVE FIT
3710 T1=0:T2=0:T3=0:T4=0:T5=0:T6=0
3720 FOR I=1 TO IL
3730 DF(I)=2*(FLB(1)-FLB(I))/(FLB(1)+FLB(I))
3740 T1=T1+DF(I)*DF(I)
3750 T2=T2+DF(I)
3760 T3=T3+LB(I)
3770 T4=T4+DF(I)*LB(I)
3780 NEXT I
3790 A=(T1*T3-T2*T4)/(IL*T1-T2*T2)
3800 B=(IL*T4-T2*T3)/(IL*T1-T2*T2)
3810 FOR I=1 TO IL
3820 T5=T5+(LB(I)-A-B*DF(I))  2
3830 T6=T6+(LB(I)-T3/IL)  2
3840 NEXT I
3850 R2=1-T5/T6
3860 RETURN
4000' TRACK AND DISPLAY ROUTINE
4005 NR=50
4010 F0=FL(1)
4015 IL=0
4020 OC=HN(1)-GS %
4030 GOSUB 310
4040 GOSUB 3320
4050 CLS
4051 LOCATE 1,5
4053 PRINT "PRESS 'F' TO RETURN TO THE
     MENU";
4055 LOCATE 2,5
4057 PRINT "K IS";KF; "REFERENCE K IS";KLB
4060 GOSUB 2500
4070 F0=F0-VO/M/85.8993
4080 GOSUB 310
4082 LOCATE 4,4
4085 PRINT "LOAD", "FREQUENCY", "TIME
     (ns)";
4090 LOCATE 5,4
4095 LD=A+B*2*(F0LB-F0)/(F0LB+F0)
4096 TOF=INT(1E+10*(OC+GS %- KLB )/F0)/10
4100 PRINT INT(LD),F0,TOF;
4105 N$=INKEY$
4110 IF N$="F" THEN CLS:RETURN
4130 GOTO 4060
4190 RETURN
4200' ESTIMATE REP RATE AND SAMPLE
     HOLD
4220 INPUT "ENTER BOLT LENGTH (IN-
     CHES)";BL
4222 PRINT
4223 PRINT "DEFAULT VALUE IS VELOCITY
     IN STEEL"
4225 PRINT "V(STEEL)=2.32E5 INCHES PER
     SECOND"
4230 INPUT "ENTER SOUND VELOCITY IN
     BOLT (INCHES PER SECOND)";VM
4235 IF VM=0 THEN VM=232000!
4240 OCLB=INT(2*BL*F0/VM)
4250 RR %=INT(OCLB/10+1)
4260 GOSUB 3220
4270 GOSUB 3220
4280 RETURN
4300' SET UP NEW BOLT
4310 GOSUB 300
4320 GOSUB 480
4330 GOSUB 4200
4340 GOSUB 900
4350 GOSUB 3500
4360 GOSUB 2200
4370 GOSUB 700
4372 F0=FL(1):OC=HN(1)-GS %
4374 GOSUB 310
4376 GOSUB 3320
4380 GOSUB 850
4390 GOSUB 2700
4395 RETURN
4400' READ OLD BOLT
4420 GOSUB 2800
4430 GOSUB 900
4440 GOSUB 3500
4450 F0=F0*OCLB/OC
4455 GOSUB 310
4460 OC=OCLB
4465 GOSUB 3320
4470 GOSUB 600
4480 GOSUB 4000
4490 RETURN
```

I claim:

1. A pulsed phase locked loop system comprising:
a frequency generator generating an output frequency signal and a reference signal, the output signal and the reference signal having the same frequency;
a transmitting gate for gating the output frequency signal of said frequency generator, the gated frequency signal driving a transmitting transducer which transmits an acoustic wave through a material;

a sample/hold for sampling a signal received by a receiving transducer, the received signal indicative of the wave transmitted through the material by the transmitting transducer; and divide-by-n counters for controlling the gating of said transmitting gate and the sampling of said sample/hold in response to the reference signal of said frequency generator, said divide-by-n counters establishing (1) a gating frequency of F/h, wherein F is the output frequency signal of said frequency generator and h is a selected integer and (2) a sampling delay of F/n wherein n is a selected integer; wherein said frequency generator adjusts its output frequency signal to maintain the phase of the gated frequency signal, the change in frequency of the output signal being indicative of the load condition of the material.

2. A method of determining load of a bearing member using a phase locked loop system which provides (a) an adjustable output frequency signal; (b) a reference signal having the same frequency F as the output frequency signal; (c) an adjustable gating integer h which is used to gate the output frequency signal at a frequency F/h prior to the output frequency being converted into an acoustic wave which is transmitted through the bearing member via a transducer acoustically coupled and received as a received signal by the transducer acoustically coupled thereto and (d) an adjustable sampling integer n to sample the received signal at a delay of F/n, wherein the phase locked loop system in a locked condition adjusts the frequency of the output frequency signal and reference signal such that a phase difference between the received signal and the reference signal is zero; the method comprising the steps of:

(1) adjusting the sampling and gating integer n to an initial value of $n_1$;
(2) locking the phase locked loop system to produce output frequency and reference signals having an initial frequency $F_1$;
(3) unlocking the phase locked loop system;
(4) advancing the initial integer $n_1$ by one such that $n_2 = n_1 + 1$;
(5) locking the phase locked loop system to produce output and reference frequency signals having a frequency $F_2 = F_1 + F_1/n_2$;
(6) computing and storing a value k defined as $INT[(F_1 n_2 - F_2 n_1)/(F_1 - F_2)]$;

wherein steps (1)–(6) occur prior to a decouplement of the transmitting and receiving transducer from the bearing member and the following steps (7)–(15) occur after the same or another transducer is acoustically coupled to the bearing member;

(7) adjusting the integer n to $n_x = n_1$;
(8) locking the phase locked loop to produce output and reference frequency signals having a frequency $F_x$;
(9) unlocking the phase locked loop system;
(10) advancing the integer $n_x$ by one such that $n_{x+1} = n_x + 1$;
(11) locking the phase locked loop system to produce output and reference frequency signals having a frequency $F_{x+1} = F_x + F_x/(n_x + 1)$;
(12) computing a value $k_x$ defined as $(F_x n_{x+1} - F_{x+1} n_x)/(F_x - F_{x+1})$;
(13) comparing $INT[k_x]$ to the previously computed and stored value of $INT[k]$;
(14) repeating steps (10)–(13) until $INT[k_x]$ approximates $INT[k]$; and
(15) calculating the load on the bearing member as a function of $F_x$.

3. A method of determining load of a bearing member using a phase locked loop system which provides (a) an adjustable output frequency signal; (b) a reference signal having the same frequency F as the output frequency signal; (c) an adjustable gating integer h which is used to gate the output frequency signal at a frequency F/h prior to the output frequency being converted into an acoustic wave which is transmitted through the bearing member via a transducer acoustically coupled and received as a received signal by the transducer acoustically coupled thereto and (d) an adjustable sampling integer n to sample the received signal at a delay of F/n, wherein the phase locked loop system in a locked condition adjusts the frequency of the output frequency signal and reference signal such that a phase difference between the received signal and the reference signal is zero; the method comprising the steps of:

(1) adjusting the sampling and gating integer n to an initial value of $n_1$;
(2) locking the phase locked loop system to produce output frequency and reference signals having an initial frequency $F_1$;
(3) unlocking the phase locked loop system;
(4) advancing the initial integer $n_1$ by one such that $n_2 = n_1 + 1$;
(5) locking the phase locked loop system to produce output and reference frequency signals having a frequency $F_2 = F_1 + F_1/n_2$;
(6) computing and storing a value k defined as $INT[(F_1 n_2 - F_2 n_1)/(F_1 - F_2)]$;

wherein steps (1)–(6) occur prior to a decouplement of the transmitting and receiving transducer from the bearing member and the following steps (7)–(15) occur after the same or another transducer is acoustically coupled to the bearing member;

(7) adjusting the integer n to $n_x = n_1$;
(8) locking the phase locked loop to produce output and reference frequency signals having a frequency $F_x$;
(9) unlocking the phase locked loop system;
(10) advancing the integer $n_x$ by one such that $n_{x+1} = n_x + 1$;
(11) locking the phase locked loop system to produce output and reference frequency signals having a frequency $F_{x+1} = F_x + F_x/(n_x + 1)$
(12) computing a value $k_x$ defined as $(F_x n_{x+1} - F_{x+1} n_x)/(F_x - F_{x+1})$;
(13) computing a difference between k and $k_x$;
(14) correcting $k_x$ based on this computed difference to equal k; and
(15) calculating the load on the bearing member as a function of $F_x$.

4. A method of calibrating a subject transducer for use with a phase locked loop system which provides (a) an adjustable output frequency signal; (b) a reference signal having the same frequency F as the output frequency signal; (c) an adjustable gating integer h which is used to gate the output frequency signal at F/h prior to the output frequency being converted into an acoustic wave via the subject transducer, transmitted through a bearing member, received and converted by the subject transducer into a received signal, and (d) an adjustable sampling integer n used to sample the received signal at a delay of F/n; wherein the phase locked loop system in a locked condition adjusts the frequency of the output frequency signal and reference signal such that the phase difference between the received signal and the reference signal is zero, the method comprising the steps of:

(1) providing a standard reference material having a constant propagation path for the acoustic wave transmitted by the subject transducer;

(2) coupling the subject transducer to the standard reference material and the phase locked loop system;

(3) calculating a calibration factor $\beta'(F_P)$ for a particular frequency $F_P$ by the following $$n_P - \frac{(n_1 - n_N)}{(F_1 - F_N)} F_P - INT\left[\frac{F_1 n_N - F_N n_1}{F_1 - F_N}\right]$$

wherein $n_P$ is a sampling integer of the phase locked loop system which produces output and reference signals having the frequency $F_P$ when the phase locked loop system is locked; $n_1$ is an initial sampling integer of the pulsed locked loop system which produces output and reference signals having frequency $F_1$; and $n_N$ is an Nth sampling integer which produces output and reference signals having frequency $F_N$, wherein N is an integer value.

5. A method of calibrating a subject transducer for use with a phase locked loop system which provides (a) an adjustable output frequency signal; (b) a reference signal having the same frequency F as the output frequency signal; (c) an adjustable gating integer h which is used to gate the output frequency signal at F/h prior to the output frequency being converted into an acoustic wave via the subject transducer, transmitted through a bearing member, received and converted by the subject transducer into a received signal, and (d) a sampling integer n used to sample the received signal at a delay of F/n; wherein the phase locked loop system in a locked condition adjusts the frequency of the output frequency signal and reference signal such that the phase difference between the received signal and the reference signal is zero, the method comprising the steps of:

(1) providing a standard reference material having a constant propagation path for the acoustic wave transmitted by the subject transducer;

(2) coupling the subject transducer to the standard reference material and the phase locked loop system;

(3) calculating a calibration factor $\beta'(F_P)$ for a particular frequency $F_P$ by the following $$n_P - \frac{(n_1 - n_N)}{(F_1 - F_N)} F_P - INT\left[\frac{F_1 n_N - F_N n_1}{F_1 - F_N}\right]$$

wherein $n_P$ is a sampling integer of the phase locked loop system which produces output and reference signals having the frequency $F_P$ when the phase locked loop system is locked; $n_1$ is an initial sampling integer of the pulsed locked loop system which produces output and reference signals having frequency $F_1$; and $n_N$ is an Nth sampling and gating integer which produces output and reference signals having frequency $F_N$, wherein N is an integer value; and (4) determining a time-of-flight of the acoustic wave at a particular frequency F by the following[1]

$$\frac{n - k - B'(F)}{F},$$

wherein the time-of-flight is indicative of the stress in the bearing member.

* * * * *